United States Patent
Abel et al.

(10) Patent No.: US 9,587,116 B2
(45) Date of Patent: Mar. 7, 2017

(54) AZO DIRECT DYES AND METHOD FOR DYEING HAIR USING THESE DYES

(71) Applicant: Noxell Corporation, Hunt Valley, MD (US)

(72) Inventors: Heike Gertrud Abel, Eiterfeld (DE); Armin Osan, Bebra (DE); Markus Speckbacher, Mettenheim (DE); Ingo Reinhold Weber, Basel (DE)

(73) Assignee: Noxell Corporation, Hunt Valley, MD (US)

( * ) Notice: Subject to any disclaimer, the term of this patent is extended or adjusted under 35 U.S.C. 154(b) by 0 days.

(21) Appl. No.: 14/926,151

(22) Filed: Oct. 29, 2015

(65) Prior Publication Data

US 2016/0122546 A1    May 5, 2016

Related U.S. Application Data

(60) Provisional application No. 62/074,946, filed on Nov. 4, 2014.

(51) Int. Cl.
| | |
|---|---|
| *A61Q 5/10* | (2006.01) |
| *C09B 29/01* | (2006.01) |
| *A61K 8/41* | (2006.01) |
| *C09B 44/10* | (2006.01) |
| *C09B 62/008* | (2006.01) |

(Continued)

(52) U.S. Cl.
CPC .......... *C09B 29/0003* (2013.01); *A61K 8/411* (2013.01); *A61Q 5/10* (2013.01); *C09B 26/06* (2013.01); *C09B 29/0808* (2013.01); *C09B 29/0813* (2013.01); *C09B 44/101* (2013.01); *C09B 56/20* (2013.01);

(Continued)

(58) Field of Classification Search
CPC .......... C09B 29/003; A61Q 5/10; A61K 8/411
USPC .......................................................... 8/405
See application file for complete search history.

(56) References Cited

U.S. PATENT DOCUMENTS

| | | |
|---|---|---|
| 2,273,564 A | 2/1942 | Dickey |
| 2,528,378 A | 10/1950 | Mannheimer |

(Continued)

FOREIGN PATENT DOCUMENTS

| | | |
|---|---|---|
| CA | 2576189 A1 | 6/2007 |
| CN | 104744272 | 7/2015 |

(Continued)

OTHER PUBLICATIONS

STIC Search Report dated Jan. 12, 2016.*

(Continued)

*Primary Examiner* — Eisa Elhilo
(74) *Attorney, Agent, or Firm* — Schwegman Lundberg & Woessner, P.A.

(57) ABSTRACT

A compound of formula (I) or (II) or (III):

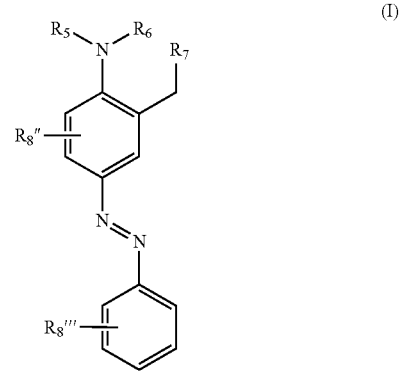

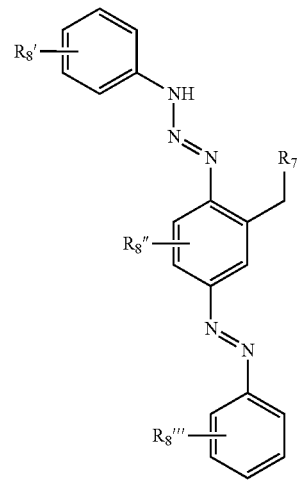

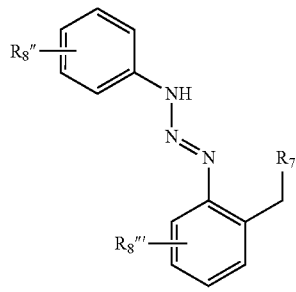

wherein $R_5$, $R_6$, $R_7$, $R_8'$, $R_8''$ and $R_8'''$ are as defined herein. This compound can be used in a composition for the dyeing of fibers.

19 Claims, No Drawings

(Continued)

(51) Int. Cl.

| | | |
|---|---|---|
| C09B 26/06 | (2006.01) | |
| C09B 29/08 | (2006.01) | |
| C09B 56/20 | (2006.01) | |

(52) U.S. Cl.
CPC .. *C09B 62/0081* (2013.01); *A61K 2800/4324* (2013.01); *A61K 2800/72* (2013.01)

(56) References Cited

U.S. PATENT DOCUMENTS

| | | | |
|---|---|---|---|
| 2,781,354 | A | 2/1957 | Mannheimer |
| 4,976,742 | A | 12/1990 | Rose |
| 4,997,451 | A | 3/1991 | Clausen |
| 6,503,282 | B1 | 1/2003 | Braun |
| 6,648,923 | B1 | 11/2003 | Goettel |
| 7,591,860 | B2 | 9/2009 | Sabelle |
| 7,611,545 | B2 * | 11/2009 | Guerin .................. A61Q 5/065 8/405 |
| 7,985,266 | B2 | 7/2011 | Zhang |
| 7,988,740 | B2 | 8/2011 | Zhang |
| 8,444,709 | B2 | 5/2013 | Lim |
| 8,444,710 | B2 | 5/2013 | Lim |
| 8,444,711 | B2 | 5/2013 | Lim |
| 8,444,712 | B2 | 5/2013 | Lim |
| 8,444,713 | B2 | 5/2013 | Lim |
| 8,444,714 | B2 | 5/2013 | Lim |
| 8,460,392 | B2 | 6/2013 | Lim |
| 2010/0031453 | A1 | 2/2010 | Greaves |
| 2012/0078016 | A1 | 3/2012 | Gardlik |
| 2012/0130128 | A1 | 5/2012 | Goettel |
| 2012/0142969 | A1 | 6/2012 | Gardlik |
| 2013/0081647 | A1 | 4/2013 | Vohra |

FOREIGN PATENT DOCUMENTS

| | | |
|---|---|---|
| DE | 20107481 U1 | 7/2001 |
| DE | 102008061864 A1 | 10/2010 |
| EP | 0052511 | 5/1982 |
| EP | 1166749 B1 | 10/2005 |
| EP | 1765267 B1 | 1/2010 |
| FR | 2946648 A1 | 12/2010 |
| FR | 2945726 B1 | 6/2011 |
| FR | 2945731 B1 | 6/2011 |
| FR | 2945732 B1 | 6/2011 |
| FR | 2945734 B1 | 6/2011 |
| FR | 2945735 B1 | 6/2011 |
| FR | 2945736 B1 | 6/2011 |
| FR | 2945737 B1 | 6/2011 |
| FR | 2945740 B1 | 6/2011 |
| FR | 2945741 B1 | 6/2011 |
| FR | 2945744 B1 | 6/2011 |
| FR | 2946647 B1 | 6/2011 |
| FR | 2945738 B1 | 7/2011 |
| FR | 2945739 B1 | 7/2011 |
| FR | 2945756 B1 | 8/2011 |
| FR | 2945727 B1 | 8/2012 |
| FR | 2945733 B1 | 8/2012 |
| FR | 2945742 B1 | 8/2012 |
| FR | 2945743 B1 | 9/2012 |
| FR | 2945728 B1 | 10/2012 |
| FR | 2945729 B1 | 10/2012 |
| FR | 2945730 B1 | 10/2012 |
| WO | WO2010133573 A2 | 11/2010 |
| WO | WO2010133575 A2 | 11/2010 |
| WO | WO2010133639 A1 | 11/2010 |
| WO | WO2010133640 A2 | 11/2010 |
| WO | WO2010133803 A1 | 11/2010 |
| WO | WO2010133804 A2 | 11/2010 |
| WO | WO2010133805 A1 | 11/2010 |
| WO | WO2010139878 A2 | 12/2010 |
| WO | WO2010142776 A1 | 12/2010 |
| WO | WO2010142777 A1 | 12/2010 |

OTHER PUBLICATIONS

International Search Report and Written Opinion, PCT/2015/058045, date of mailing Apr. 22, 2016.
Encyclopedia of Chemical Technology, Kirk-Othmer, Third Edition, 1982, vol. 3, pp. 896-900.
Encyclopedia of Chemical Technology, Kirk-Othmer, Third Edition, 1982, vol. 15, pp. 439-458.
Polymers in Nature by E. A. MacGregor and C. T. Greenwood, published by John Wiley & Sons, Chapter 6, pp. 240-328, 1980.
Handbook of Surfactants by M. R. Porter, published by Blackie & Son (Glasgow and London), 1991, pp. 116-178.
Whistler, Roy L., Editor, "Industrial Gums—Polysaccharides and their Derivatives," Academic Press, Inc.
De Nino, A. et al.: "Synthesis of Deuterium-Labeled Azo Dyes of the Sudan Family", Synthesis, vol. 2008, No. 3, Jan. 10, 2008, pp. 459-463, XP55239996, ISSN: 0039-7881, DOI:1O.1055/S-20O8-1O32O36 Scheme 6; p. 461, p. 462; compounds (23),(24).
Rajaganesh, R. et al.: "Synthesis and Properties of Amphiphilic Photoresponsive Gelators for Aromatic Solvents", Organic Letters, vol. 14, No. 3, Jan. 17, 2012, pp. 748-751. XP55239807, ISSN: 1523-7060, DOI: 10.1021/ol203294v, Scheme 1; p. 749, col. 1; compounds (la-f).
Rajaganesh. R. et al.: "Synthesis and Properties of Amphiphilic Photoresponsive Gelators for Aromatic Solvents, Supporting Information", Organic Letters, vol. 14, No. 3, Jan. 17, 2012. pp. S1-S46, XP55240022, ISSN: 1523-7060. DOI: 10.1021/01203294v, Scheme 2.1; pp. S3-S4.
Gowda, S. et al.: "Reductive cleavage of azo compounds catalysed by comnercial zinc dust and hydrazinium monoformate as a new hydrogen donor for heterogenous catalytic transfer hydrogenation", Journal of Chemical Research—Synopses, vol. 8, 2002, pp. 384-385. XP009187898, ISSN: 0308-2342, Scheme 1; p. 384, last entry; p. 385; table 1.
Abiraj. K. Etal.: "Palladium-catalyzed simple and efficient hydrogenative cleavage of azo compounds using recyclable polymer-supported formate", Canadian Journal of Chemistry, vol. 83, No. 5, 2005, pp. 517-520, XP009187897, ISSN: 0008-4042, Entry 14; p. 518; table 1.
Geoffrey Hallas: "The Effects of Terminal Groups in 4-Aminoazobenzene and Disperse Dyes Related Thereto", Journal of the Society of Dyers and Colourists, vol. 95, No. 8, Aug. 22, 1979. pp. 285-294. XP055240311. GB ISSN: 0037-9859. DOI:10. 1 U 1 / j . 1478-4408.1979. tb03484.x, pp. 285-288; compound XII.
Leopold Horner et al: "Sterisch 1.4, behindertes Buttergelb and cancerogene Wirkung", Chemische Berichte, vol. 89, No. 12, Dec. 1, 1956, pp. 2756-2759. XP055240345, DE ISSN: 0009-2940, DOI: 10.1002/cber.19560891214, p. 2757; compounds I-III.
Griffiths John et al: "Steric Effects in 1-13 4-Dimethylaminoazobenzenes and Their Protonated Species", Jan. 1, 1981, Journal of Chemical Research. Miniprint, Scientific Reviews, Northwood, GB. pp. 3722-3739, XP008178573, ISSN: 0308-2350, p. 3726; compounds 6a,6b.
F. Jones et al: "Orientation of Dyes in 1 Liquid Crystalline Media", Journal of the Society of Dyers and Colourists, vol. 95, No. 10, Oct. 22, 1979, pp. 352-359, XP055240327, GB ISSN: 0037-9859, DOI: 10. 11U/j.1478-4408.1979, tb03433.x, table 1; compound XI.
A. Van Loon et al: "Preparation of some 1 4-dimethylaminoazobenzene derivatives with substituents in the 3- or in the 3-and the 5-position", Recueil Des Travaux Chimiques Des Pays-Bas, vol. 79, No. 9, Sep. 2, 1960, pp. 977-1001, XP055240338, Amsterdam, NL ISSN: 0165-0513, DOI: 10.1002/recl.19600790910, p. 977; compounds I-IV.
Dong Myung. Shin et al: "Solvent-induced mechanism change in charge-transfer molecules. Inversion versus rotation paths for the Z.fwdarw.E isomerization of donor-acceptor substituted azobenzenes", Journal of the American Chemical Society, vol. 110, No. 15, Jul. 1, 1988, pp. 5206-5208. XP055240347, US ISSN: 0002-7863, DOI: 10.1O21/ja00223aO58, p. 5206; compound 3.
Goebel Carsten et al: "Introduction of a methoxymethyl side chain intopphenylenediamine attenuates its sensitizing potency and reduces the risk of allergy induction", Toxicology and Applied Pharmacology, Academic Press. Amsterdam. NL, vol. 274. No. 3,

(56) References Cited

OTHER PUBLICATIONS

Dec. 10, 2013, pp. 480-487, XP028815245, ISSN: 0041-008X, DOI: 10.1016/J.Taap.2013.11.016.

* cited by examiner

AZO DIRECT DYES AND METHOD FOR DYEING HAIR USING THESE DYES

FIELD OF THE INVENTION

The present invention relates to the dyeing of keratin fibers such as, for example, human hair, using azo direct dyes.

BACKGROUND OF THE INVENTION

The permanent alteration of the hair color by the application of hair dyes is well known. In order to provide the consumer with the shade and the intensity of color desired, a complex chemical process is utilized. Permanent hair dyeing formulations typically comprise oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of color. This reaction typically takes place in an aggressive environment at approximately pH 10 in the presence of an alkalizing agent and an oxidizing agent. Typically an oxidizing composition (also called developer and/or oxidizing component) comprising the oxidizing agent and a dye composition (also called tint or dye component) comprising the alkalizing agent and if present the precursors dye molecules are mixed shortly before use. The consumer repeats this process regularly in order to maintain the desired hair color and shade and the intensity of color and to ensure continual, even coverage of the hair including coverage of new hair growth. Under application conditions some of the hair dye precursors currently used in permanent hair dyeing formulations may enter into contact with the skin of the consumer and may sometimes be responsible for skin allergy.

In order to try to overcome this problem, a new oxidative dye precursor has been developed, namely 2-methoxymethyl-p-phenylenediamine. Indeed, it has been found in previous communications and publications, that this new oxidative dye precursor shows a more favorable toxicological profile and has meanwhile been introduced as an industry standard as safe replacement for traditionally used paraphenylene diamines. While not wishing to be bound by theory it is also believed that the introduction of a methoxymethyl side chain into p-phenylenediamine may attenuate its sensitizing potency and reduce the risk of allergy induction (Toxicology and Applied Pharmacology, 274 (2014) 480-487). 2-methoxymethyl-p-phenylenediamine and its derivatives are defined according to the following formula:

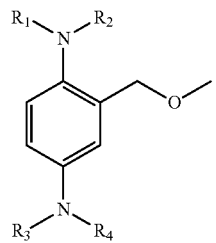

wherein $R_1$, $R_2$, $R_3$ and $R_4$ are selected, independently from each other, from the group consisting of a $C_1$-$C_6$ alkylamino group, a $C_1$-$C_6$ alkylcyano group, a $C_1$-$C_6$ alkyl group, a $C_1$-$C_6$ alkyloxy group, a benzyl group, a hydrogen atom, a $C_1$-$C_6$ hydroxyalkyl group, or a $C_4$-$C_6$-polyhydroxyalkyl group, wherein the alkyl groups may be linear or branched.

Instead of using permanent hair dyeing compositions, it is possible to use temporary or semi-permanent hair dyeing formulations which comprise direct dyes. Some of the direct dyes which are currently used in these temporary or semi-permanent hair dyeing formulations may also sometimes be responsible for skin allergy. Therefore, there is still the need of providing direct dye compounds and compositions comprising these direct dye compounds which are characterized by a reduced sensitizing potency and therefore a reduced risk of allergy induction.

Furthermore, some of the direct dyes which are currently used in these temporary or semi-permanent hair dyeing formulations may also be sensitive to the action of oxidizing agents such as hydrogen peroxide which make them generally unusable in lightening direct dye compositions comprising an oxidizing agent in combination with an alkalizing agent. Therefore, there is also still the need of providing direct dye compounds that can be used in compositions comprising an oxidizing agent in combination with an alkalizing agent.

Finally, there is also the need of providing direct dye compounds and compositions comprising these direct dye compounds which can provide the hair with a yellow or orange colour.

SUMMARY OF THE INVENTION

The present invention relates to a compound of formula (I) or (II) or (III):

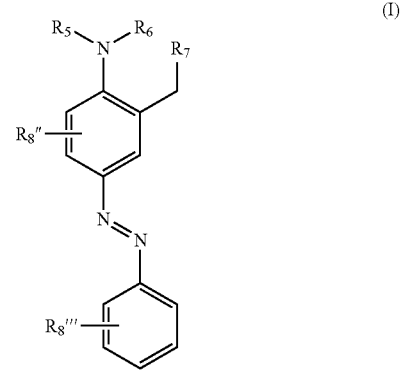

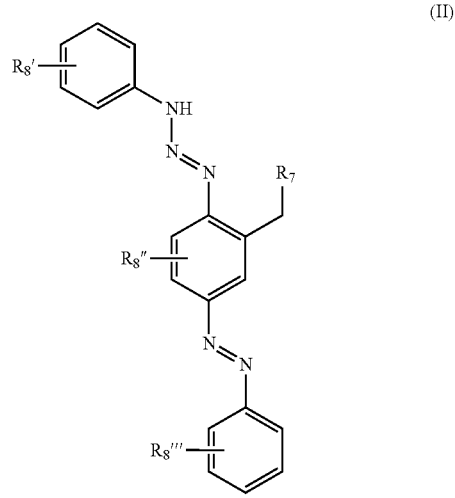

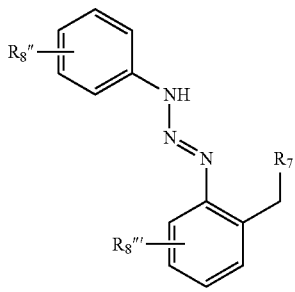

(III)

cosmetically acceptable salts thereof or mixtures thereof; wherein in formula (I), $R_5$ and $R_6$ are selected, independently from each other, from the group consisting of a $C_1$-$C_6$ alkylamino group, a $C_1$-$C_6$ alkylcyano group, a $C_1$-$C_6$ alkyl group, a $C_1$-$C_6$ alkoxy group, a benzyl group, a hydrogen atom, a $C_1$-$C_6$ hydroxyalkyl group, and a $C_4$-$C_6$ polyhydroxyalkyl group, wherein the alkyl groups are linear or branched; and wherein in formula (I) or (II) or (III), $R_7$ is selected from the group consisting of a hydrogen atom, a halogen atom, a $C_1$-$C_6$ alkyl group, a hydroxyl group, a nitro group, a cyano group, an acyl group, an aminoacyl group, and a methoxy group;

wherein in formula (I) or (II) or (III), $R_8'$, $R_8''$ and $R_8'''$ are selected, independently from each other, from the group consisting of a hydrogen atom, a halogen atom, a $C_1$-$C_6$ alkyl group, a hydroxyl group, a hydroxylamine group, a nitroso group, a nitro group, a methoxymethyl group, an acyl group, an aminoacyl group, a methoxy group and a hydroxyalkyl group.

The present invention also relates to a composition for the dyeing of fibers comprising, in a cosmetically acceptable carrier, at least one compound of formula (I) or (II) or (III) as defined hereinbefore.

Finally, the present invention also relates to a method for dyeing fibers, wherein the composition defined hereinbefore is applied to the keratin fibers.

DETAILED DESCRIPTION OF THE INVENTION

As used herein, the term "keratin" refers to a scleroprotein found in epidermal tissues and modified into hard structures such as horns, hair, and nails. As used herein, the term "hair" refers to keratinous fibers on a living, e.g. a person, or non-living body, e.g. in a wig, hairpiece, or other aggregation of non-living keratinous fibers. Mammalian, preferably human hair is preferred. Notably, hair, wool, fur, and other keratinous fibers are suitable substrates for coloring by the compounds and compositions described herein.

It is to be understood that when the description refers to a particular structure, all of the reasonable additional tautomeric structures are included. In the art, tautomeric structures are frequently represented by one single structure and the invention follows this general practice.

All ratios or percentages are weight ratios or weight percentages unless specifically stated otherwise.

Azo Direct Dye Compound(s)

The present invention relates to a compound of formula (I) or (II) or (III) as stated hereinbefore.

The compound of formula (I), (II) or (III) may comprise at least one methoxymethyl group which is attached to at least one of the phenyl groups.

At least some of the azo direct dye compounds according to the present invention may have a more favourable toxicological profile than other azo direct dye compounds. Indeed, while not wishing to be bound by theory it is believed that introducing at least one methoxymethyl group onto at least one of the phenyl groups of the compound may attenuate its sensitizing potency and reduce the risk of allergy induction in a similar manner as when a methoxymethyl side chain is added into p-phenylenediamine to obtain the 2-methoxymethyl-p-phenylenediamine oxidative dye precursor. Furthermore, also other technical applications such as the use of these dyes in fabric coloring, ink printing etc. may strongly benefit from less toxic and less sensitizing properties of the dyes. At least some of the azo direct dye compounds according to the present invention may be sufficiently stable in the presence of oxidizing agents such as hydrogen peroxide and therefore can be used in lightening direct dye compositions comprising an oxidizing agent in combination with an alkalizing agent. Finally, at least some of the azo direct dye compounds according to the present invention can provide the hair with a yellow or orange colour.

In formula (I) or (II) or (III), $R_7$ may be selected from the group consisting of hydroxyl group or methoxy group, alternatively $R_7$ may be a methoxy group.

In formula (I), $R_5$ and $R_6$ may be selected, independently from each other, from the group consisting of a hydrogen atom and a hydroxyalkyl group. The hydroxyalkyl group may be a hydroxyethyl group.

The compound of formula (I) or (II) or (III) may be selected from the group consisting of:

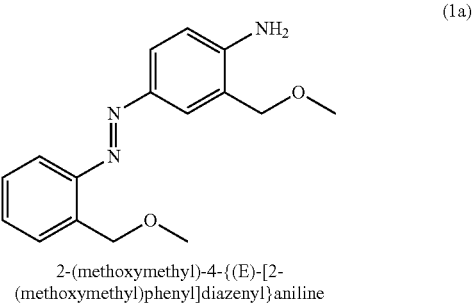

(1a)

2-(methoxymethyl)-4-{(E)-[2-(methoxymethyl)phenyl]diazenyl}aniline

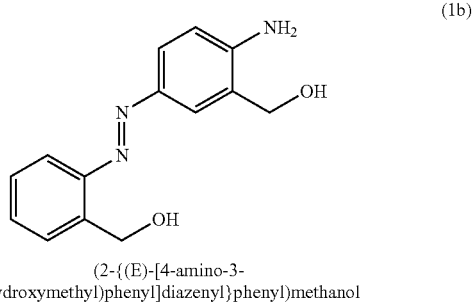

(1b)

(2-{(E)-[4-amino-3-(hydroxymethyl)phenyl]diazenyl}phenyl)methanol

-continued (1c)
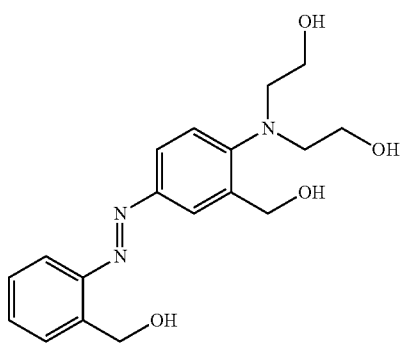

2,2'-{[2-(hydroxymethyl)-4-{(E)-[2-(hydroxymethyl)phenyl]diazenyl}phenyl]imino}diethanol (1d)
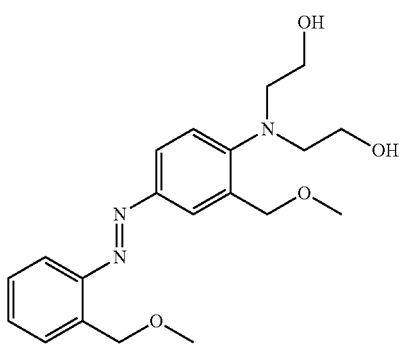

2,2'-{[2-(methoxymethyl)-4-{(E)-[2-(methoxymethyl)phenyl]diazenyl}phenyl]imino}diethanol (2a)
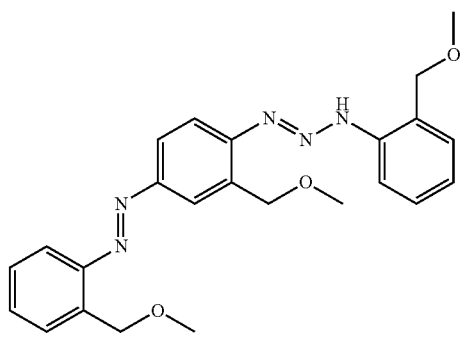

(2-{(2E)-3-[2-(methoxymethyl)-4-{(E)-[2-(methoxymethyl)phenyl]diazenyl}phenyl]triaz-2-en-1-yl}phenyl)methanol (3a)
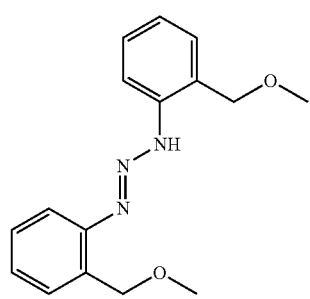

2-(methoxymethyl)-4-{3-[2-(methoxymethyl)phenyl]triaz-1-en-1-yl}aniline

Method for Obtaining the Compounds of Formula (I) or (II) or (III)

The hereinbefore azo direct dye compounds are accessible via self diazotation of ortho-substituted aniline derivatives. These compounds may be obtained following conventional synthesis techniques.

In the following section of the application, processes for the preparation of compounds according to the present invention are described.

Preparation of the 2-(methoxymethyl)-4-{(E)-[2-(methoxymethyl)phenyl]diazenyl}aniline Compound of Formula (1a), a Cosmetically Acceptable Salt Thereof, or Mixture Thereof The 2-(methoxymethyl)-4-{(E)-[2-(methoxymethyl)phenyl]diazenyl}aniline compound of formula (1a), a cosmetically acceptable salt thereof, or mixture thereof is prepared according to a process comprising the steps a), b) and optional step c) as described hereinafter.

a) synthesizing the intermediate 2-(methoxymethyl)-4-{3-[2-(methoxymethyl)phenyl]triaz-1-en-1-yl}aniline (iv) via diazotation using 2-methoxymethylaniline (ii) to obtain the intermediate of formula (iii) followed by diazo coupling between the intermediate of formula (iii) and 2-methoxymethylaniline (ii):

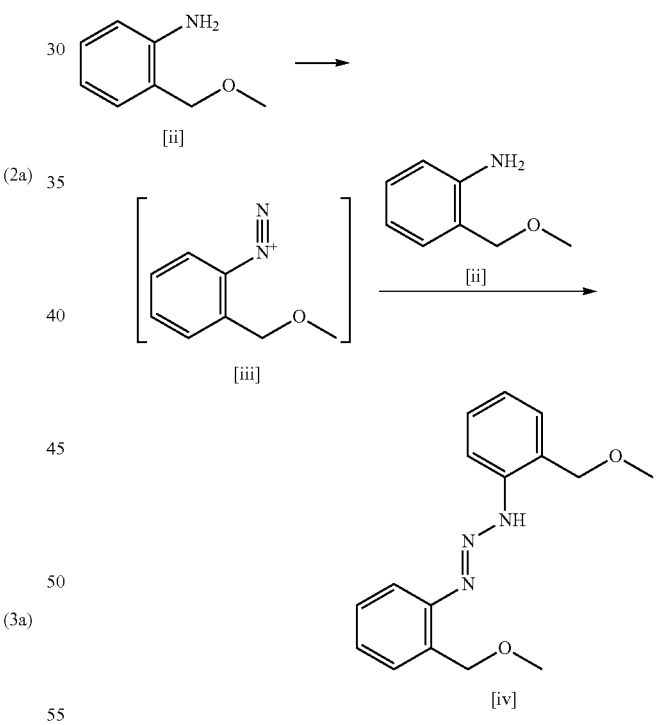

This step is carried out in the presence of at least one nitrosation agent in order to convert 2-methoxymethylaniline (ii) into the intermediate of formula (iii). The nitrosation agent(s) may be selected from the group consisting of sodium nitrite, potassium nitrite, dinitrogen pentoxide, nitrosylsulfuric acid and mixtures thereof.

This step is carried out in the presence of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Alternatively, the mineral or organic acid may be selected from the group consisting of hydrogen chloride, sulfuric acid, sulfurous acid, acetic acid and mixtures thereof. Alternatively, the mineral or organic acid may be acetic acid.

This step may be carried out in the presence of at least one radical scavenger. The radical scavenger may be selected from the group consisting of acrylonitrile, methacrylate, urea and mixtures thereof. Using at least one radical scavenger may be particularly advantageous in order to reduce the risk of formation of azotars which would negatively impact the overall yield of the compound (iv).

The solvent(s) used in this step may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, isopentanol, t-butanol, isopropanol, n-propanol, ethanol, methanol, glycols, hydrogen chloride, water and mixtures thereof, alternatively from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof, alternatively from the group consisting of n-propanol, acetic acid, propionic acid, oxalic acid, malonic acid, hydrogen chloride, sulphuric acid, phosphoric acid and mixtures thereof.

The formation of the compound of formula (1a) may be observed as a side reaction under the given reaction conditions:

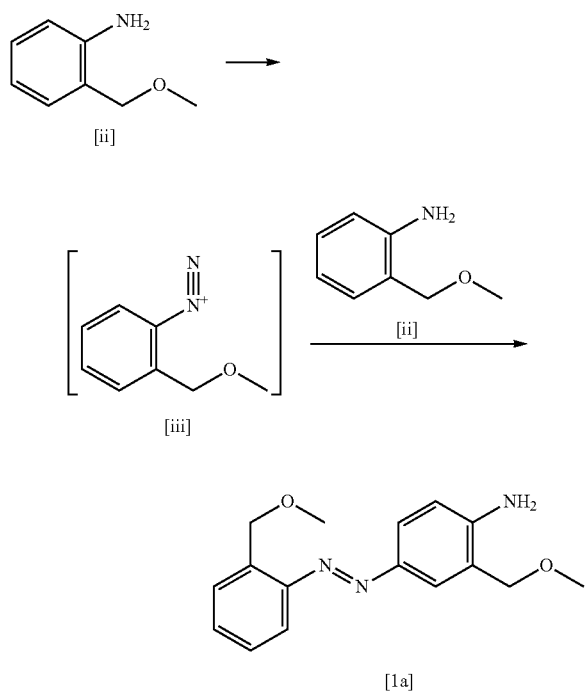

b) synthesizing the 2-(methoxymethyl)-4-{(E)-[2-(methoxymethyl)phenyl]diazenyl}aniline compound of formula (1a) via rearrangement of the intermediate 2-(methoxymethyl)-4-{3-[2-(methoxymethyl)phenyl]triaz-1-en-1-yl}aniline (iv) obtained in step a):

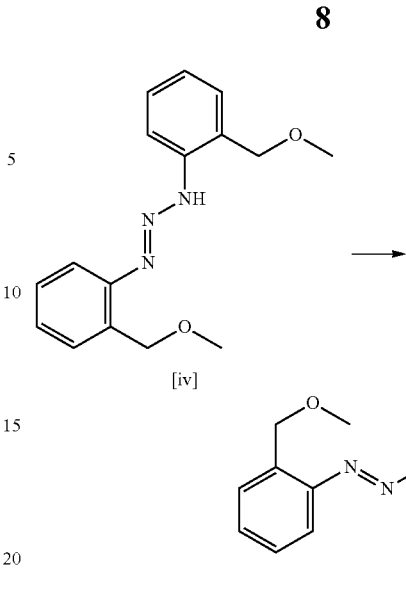

This step is carried out in the presence of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Alternatively, the mineral or organic acid may be selected from the group consisting of hydrogen chloride, sulfuric acid, sulfurous acid, acetic acid and mixtures thereof. Alternatively, the mineral or organic acid may be acetic acid.

The pH of the mixture is increased by adding a base. The base may be sodium acetate.

The solvent(s) used in this step may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, isopentanol, t-butanol, isopropanol, n-propanol, ethanol, methanol, glycols, hydrogen chloride, water and mixtures thereof, alternatively from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof, alternatively from the group consisting of n-propanol, acetic acid, propionic acid, oxalic acid, malonic acid, hydrogen chloride, sulphuric acid, phosphoric acid and mixtures thereof.

In a further step c), the compound of formula (1a) can be converted into a cosmetically acceptable salt. The cosmetically acceptable salt may be any inorganic or organic cosmetically acceptable salt. The cosmetically acceptable salt may be selected from chloride, sulfate, hydrogensulfate or malonate salt. The compound of formula (1a) may be converted into a cosmetically acceptable salt using a mineral or organic acid selected from the group consisting of hydrogen chloride, sulfuric acid, phosphoric acid, acetic acid, malic acid and mixtures thereof.

Preparation of the (2-{(E)-[4-amino-3-(hydroxymethyl)-phenyl]diazenyl}-phenyl)methanol Compound of Formula (1b), a Cosmetically Acceptable Salt Thereof, or Mixture Thereof The (2-{(E)-[4-amino-3-(hydroxymethyl)-phenyl]diazenyl}-phenyl)methanol compound of formula (1b), a cosmetically acceptable salt thereof, or mixture thereof is prepared according to a process comprising the steps a), b) and optional step c) as described hereinafter.

a) synthesizing the intermediate 2-(hydroxymethyl)-4-{3-[2-(hydroxymethyl)phenyl]triaz-1-en-1-yl}aniline (iv) via diazotation using 2-hydroxymethylaniline (ii) to obtain the intermediate of formula (iii) followed by diazo coupling between the intermediate of formula (iii) and 2-hydroxymethylaniline (ii):

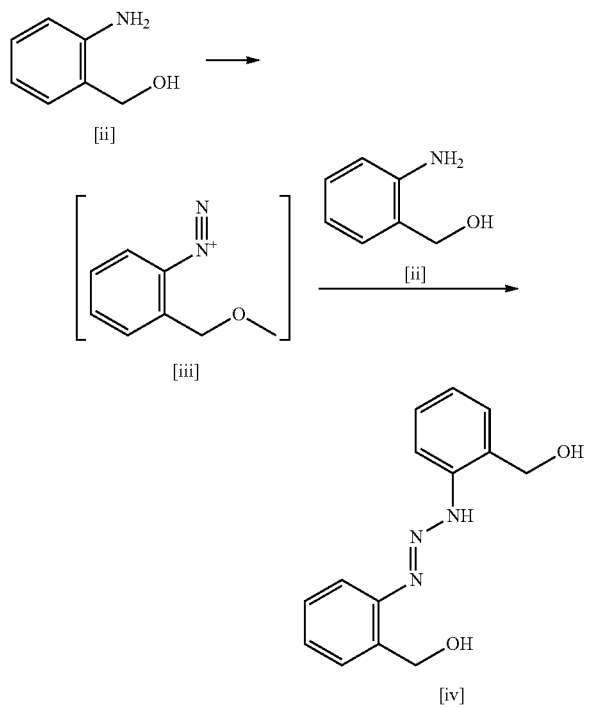

This step is carried out in the presence of at least one nitrosation agent in order to convert 2-hydroxymethylaniline (ii) into the intermediate of formula (iii). The nitrosation agent(s) may be selected from the group consisting of sodium nitrite, potassium nitrite, dinitrogen pentoxide, nitrosylsulfuric acid and mixtures thereof.

This step is carried out in the presence of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Alternatively, the mineral or organic acid may be selected from the group consisting of hydrogen chloride, sulfuric acid, sulfurous acid, acetic acid and mixtures thereof. Alternatively, the mineral or organic acid may be acetic acid.

This step may be carried out in the presence of at least one radical scavenger. The radical scavenger may be selected from the group consisting of acrylonitrile, methacrylate, urea and mixtures thereof. Using at least one radical scavenger may be particularly advantageous in order to reduce the risk of formation of azotars which would negatively impact the overall yield of the compound (iv).

The solvent(s) used in this step may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, isopentanol, t-butanol, isopropanol, n-propanol, ethanol, methanol, glycols, hydrogen chloride, water and mixtures thereof, alternatively from the group consisting of n-butanol, isopropanol, n-propanol, ethanol, methanol, acetic acid, propionic acid, oxalic acid, malonic acid, hydrogen chloride, sulphuric acid, phosphoric acid_and mixtures thereof, alternatively from the group consisting of n-propanol, acetic acid, propionic acid, oxalic acid, malonic acid, hydrogen chloride, sulphuric acid, phosphoric acid and mixtures thereof.

b) synthesizing the intermediate 2-(hydroxymethyl)-4-{(E)-[2-(hydroxymethyl)phenyl]diazenyl}aniline (1b) via rearrangement of the intermediate 2-(hydroxymethyl)-4-{3-[2-(hydroxymethyl)phenyl]triaz-1-en-1-yl}aniline (iv) obtained in step a):

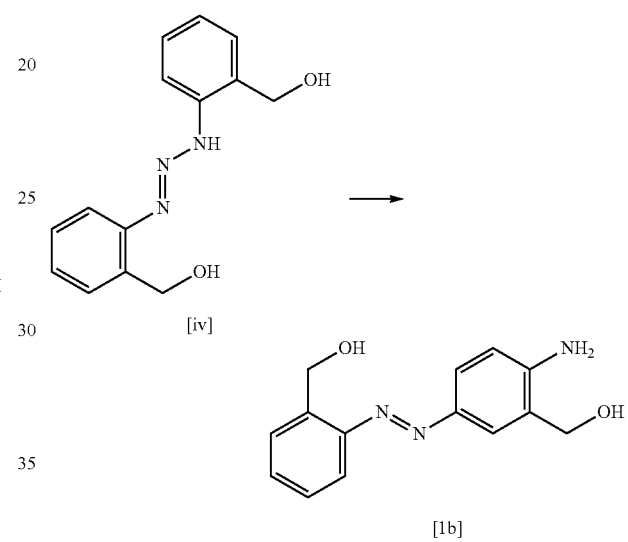

This step is carried out in the presence of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Alternatively, the mineral or organic acid may be selected from the group consisting of hydrogen chloride, sulfuric acid, sulfurous acid, acetic acid and mixtures thereof. Alternatively, the mineral or organic acid may be acetic acid.

The pH of the mixture is increased by adding a base. The base may be sodium acetate.

The solvent(s) used in this step may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, isopentanol, t-butanol, isopropanol, n-propanol, ethanol, methanol, glycols, hydrogen chloride, water and mixtures thereof, alternatively from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof, alternatively from the group consisting of n-propanol, acetic acid, propionic acid, oxalic acid, malonic acid, hydrogen chloride, sulphuric acid, phosphoric acid and mixtures thereof.

In a further step c), the compound of formula (1b) can be converted into a cosmetically acceptable salt. The cosmetically acceptable salt may be any inorganic or organic cosmetically acceptable salt. The cosmetically acceptable salt may be selected from chloride, sulfate, hydrogensulfate or malonate salt. The compound of formula (1b) may be converted into a cosmetically acceptable salt using a mineral or organic acid selected from the group consisting of hydrogen chloride, sulfuric acid, phosphoric acid, acetic acid, malic acid and mixtures thereof.

Preparation of the (2-{(2E)-3-[2-(methoxymethyl)-4-{(E)-[2-(methoxymethyl)phenyl]diazenyl}phenyl]triaz-2-en-1-yl}phenyl)methanol Compound of Formula (2a), a Cosmetically Acceptable Salt Thereof, or Mixture Thereof via Diazotation of 2-methoxymethylaniline (ii) with Half Molar Equivalents of Non Diazotized 2-methoxymethylaniline (ii)

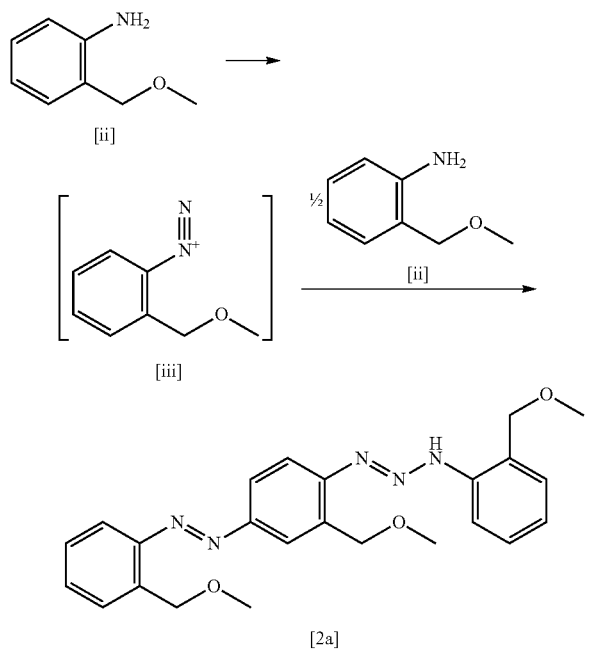

acid, malonic acid, sulphuric acid, phosphoric acid, isopentanol, t-butanol, isopropanol, n-propanol, ethanol, methanol, glycols, hydrogen chloride, water and mixtures thereof. Alternatively, the solvent(s) used in this step may be selected from the group consisting of n-butanol, water and mixture thereof.

Preparation of the 2-(methoxymethyl)-4-{3-[2-(methoxymethyl)phenyl]triaz-1-en-1-yl}aniline Compound of Formula (3a), a Cosmetically Acceptable Salt Thereof, or Mixture Thereof via Diazotation Using 2-methoxymethylaniline (ii) to Obtain the Intermediate of Formula (iii) Followed by Diazo Coupling Between the Intermediate of Formula (iii) and 2-methoxymethylaniline (ii)

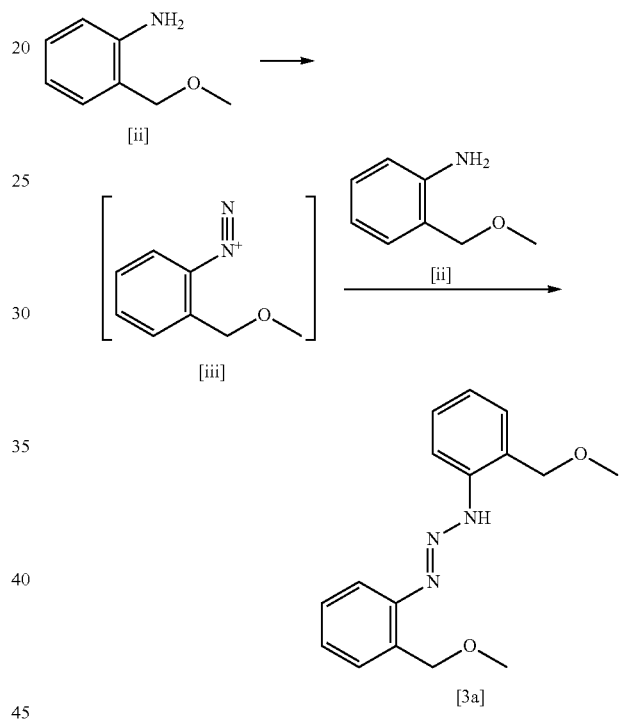

This step is carried out in the presence of at least one nitrosation agent in order to convert 2-methoxymethylaniline (ii) into the intermediate of formula (iii). The nitrosation agent(s) may be selected from the group consisting of sodium nitrite, potassium nitrite, dinitrogen pentoxide, nitrosylsulfuric acid and mixtures thereof.

This step is carried out in the presence of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Alternatively, the mineral or organic acid may be selected from the group consisting of hydrogen chloride, sulfuric acid, sulfurous acid, acetic acid and mixtures thereof. Alternatively, the mineral or organic acid may be acetic acid.

This step may be carried out in the presence of at least one radical scavenger. The radical scavenger may be selected from the group consisting of acrylonitrile, methacrylate, urea and mixtures thereof. Using at least one radical scavenger may be particularly advantageous in order to reduce This step is carried out in the presence of at least one nitrosation agent in order to convert 2-methoxymethylaniline (ii) into the intermediate of formula (iii). The nitrosation agent(s) may be selected from the group consisting of sodium nitrite, potassium nitrite, dinitrogen pentoxide, nitrosylsulfuric acid and mixtures thereof.

This step is carried out in the presence of at least one mineral or organic acid. The mineral or organic acid may be selected from the group consisting of hydrogen chloride, trifluoroacetic acid, sulfuric acid, sulfurous acid, carbonic acid, nitric acid, acetic acid, propionic acid, phosphoric acid and mixtures thereof. Alternatively, the mineral or organic acid may be selected from the group consisting of hydrogen chloride, acetic acid and mixture thereof.

The solvent(s) used in this step may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic the risk of formation of azotars which would negatively impact the overall yield of the compound (iv).

The solvent(s) used in this step may be selected from the group consisting of 1,2-dimethoxyethane, pentane, cyclopentane, hexane, cyclohexane, benzene, toluene, 1,4-dioxane, diethyl ether, tetrahydrofuran, methyl-tetrahydrofuran, n-pentanol, n-butanol, acetic acid, propionic acid, oxalic acid, malonic acid, sulphuric acid, phosphoric acid, isopentanol, t-butanol, isopropanol, n-propanol, ethanol, methanol, glycols, hydrogen chloride, water and mixtures thereof, alternatively from the group consisting of n-butanol, isopropanol, n-propanol, ethanol, methanol, acetic acid, propionic acid, oxalic acid, malonic acid, hydrogen chloride, sulphuric acid, phosphoric acid and mixtures thereof, alternatively from the group consisting of n-propanol, acetic acid, propionic acid, oxalic acid, malonic acid, hydrogen chloride, sulphuric acid, phosphoric acid and mixtures thereof.

Composition Comprising Azo Direct Dye Compound(s)

The present invention also relates to a composition for the dyeing of fibers comprising in a cosmetically acceptable carrier, at least one compound of formula (I) or (II) or (III) as defined hereinbefore. The composition may be a composition for the dyeing of keratin fibers or synthetic fibers.

The composition may comprise a total amount of compound(s) of formula (I) or (II) or (III) ranging from 0.0001% to 10%, alternatively from 0.0001% to 5%, alternatively from 0.0001% to 4% by total weight of the composition.

Cosmetically Acceptable Carrier

The composition comprises a cosmetically acceptable carrier. The cosmetically acceptable carrier may be selected from water, or a mixture of water and at least one organic solvent to dissolve the compounds that would not typically be sufficiently soluble in water.

Suitable organic solvents include, but are not limited to: $C_1$ to $C_4$ lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

The cosmetically acceptable carrier may be selected from the group consisting of water, ethanol, propanol, isopropanol, glycerol, 1,2-propylene glycol, hexylene glycol, ethoxy diglycol, and mixtures thereof.

The composition may comprise water as a main ingredient, particularly in a total amount of less than 70%, or less than 50% or less than 30%, by total weight of the composition. Typically, when present, the composition comprises a total amount of organic solvents ranging from 1% to 30%, by total weight of the composition.

The composition may comprise further ingredients in order to further enhance the properties of the composition, as long as these are not excluded by the claims.

Suitable further ingredients include, but not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Direct Dye(s)

The composition may further comprise at least one additional direct dye in addition to the compounds of formula (I) or (II) or (III) as defined hereinbefore.

The composition may comprise a total amount of direct dyes including the compound of formula (I) or (II) or (III) ranging from 0.0001% to 10%, alternatively from 0.0001% to 5%, alternatively from 0.0001% to 4% by total weight of the composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

Oxidizing Agent(s)

The composition may comprise at least one oxidizing agent. Any oxidizing agent known in the art may be used. Preferred oxidizing agents are water-soluble peroxygen oxidizing agents. As used herein, "water-soluble" means that in standard conditions at least about 0.1 g, preferably about 1 g, more preferably about 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft.

The composition may comprise a total amount of oxidizing agent(s) ranging from 0.1% to 10%, alternatively from 1% to 7%, alternatively from 2% to 5%, by total weight of the composition. The amount of each particular oxidizing agent or mixtures thereof described hereinafter can account for up to 100% (or 100%) of the total amount of oxidizing agent(s) in the composition.

Suitable water-soluble oxidizing agents include, but are not limited to: inorganic peroxygen materials capable of yielding hydrogen peroxide in an aqueous solution.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agent(s) can be used if desired. The oxidizing agent(s) may be provided in aqueous solution or as a powder which is dissolved prior to use.

The composition may comprise at least one water-soluble oxidizing agent(s) selected from the group consisting of hydrogen peroxide, percarbonates, persulphates, and mixtures thereof. A potential oxidizing agent for use herein is a source of peroxymonocarbonate ions formed in situ from a source of hydrogen peroxide and a hydrogen carbonate ion source. Moreover, this system is also particularly effective in combination with a source of ammonia or ammonium ions. Accordingly, any source of these peroxymonocarbonate ions may be used. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may be used both as an oxidizing agent and as a source of carbonate ions. Preferred sources of carbonate ions, carbamate and hydrocarbonate ions are sodium hydrogen carbonate, potassium hydrogen carbonate, ammonium carbamate, and mixtures thereof.

Alkalizing Agent(s)

The composition may comprise at least one alkalizing agent. Any alkalizing agent(s) known in the art may be used. Typically, the composition may comprise a total amount of alkalizing agents ranging from 0.1% to 10%, alternatively from 0.5% to 6%, alternatively from 1% to 4%, by total weight of the composition. The amount of each particular alkalizing agent or mixtures thereof described hereinafter can account for up to 100% (or 100%) of the total amount of alkalizing agent(s) in the composition.

The alkalizing agent(s) may be selected from the group consisting of ammonia, ammonium hydroxide, ammonium carbonate, alkanolamines (such as monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol), guanidium salts, alkali metal hydroxides (such as sodium hydroxide), alkali metal carbonates and mixtures thereof. Alternatively, the alkalizing agent (s) may be selected from the group consisting of ammonia, ammonium hydroxide, monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof. Alternatively, the alkalizing agent may be monoethanolamine Preferably, if present, the ammonium ions and carbonate ions are present in the composition at a weight ratio of from 3:1 to 1:10, alternatively from 2:1 to 1:5.

The composition may be substantially free of ammonia. The term "substantially free of ammonia" means that the composition of the present invention is either completely free of ammonia (including ammonium ions) or contains no appreciable amount of ammonia (including ammonium ions), for example, no more than 1%, or no more than 0.5%, or no more than 0.3%, or no more than 0.1%, by total weight of the composition. In the embodiments wherein the composition is substantially free of ammonia, the composition may comprise an alkanolamine such as monoethanolamine.

pH Modifiers and Buffering Agents

The composition may further comprise, instead of or in addition to the alkalizing agent(s), a pH modifier and/or buffering agent in an amount that is sufficiently effective to adjust the pH of the composition to fall within a range from 1.5 to 11, alternatively from 2 to 10, alternatively from 2.2 to about 9.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulants (such as inorganic and inorganic acids including for example phosphoric acid, acetic acid, ascorbic acid, citric acid or tartaric acid, hydrochloric acid); and mixtures thereof.

Thickeners and/or Rheology Modifiers

The composition may further comprise at least one thickener in an amount sufficient to provide the composition with a viscosity so that it can be readily applied to the hair without unduly dripping off the hair and causing mess.

The composition may comprise a total amount of thickener(s) ranging from at least 0.1%, alternatively at least 0.5%, alternatively at least 1%, by total weight of the composition.

Suitable thickeners include, but are not limited to: associative polymers, polysaccharides, non-associative polycarboxylic polymers, and mixtures thereof.

Carbonate Ion Sources

The composition may further comprise a source of carbonate ions, carbamate ions, hydrogen carbonate ions, and mixtures thereof in a sufficient amount to reduce damage to the hair during the coloring process.

The composition may comprise a total amount of a carbonate ion source ranging from 0.1% to 15%, alternatively from 0.1% to 10%, alternatively from 1% to 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof; alternatively ammonium carbonate, ammonium hydrogen carbonate, and mixtures thereof.

Conditioning Agents

The composition may further comprise at least one conditioning agent, and/or be used in combination with a composition comprising at least one conditioning agent.

The composition may comprise a total amount of conditioning agent(s) ranging from 0.05% to 20%, alternatively from 0.1% to 15%, alternatively from 0.2% to 10%, alternatively from 0.2% to 2%, alternatively from 0.5% to 2%, by total weight of the composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol.

Surfactants

The composition may further comprise at least one surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

Typically, the composition may comprise a total amount of surfactants ranging from 1% to 60%, alternatively from 2% to 30%, alternatively from 8% to 25%, alternatively from 10% to 20%, by weight of the total composition.

The compositions may comprise a mixture of an anionic surfactant and an amphoteric surfactant with one or more nonionic surfactants. The composition may comprise a total amount of anionic surfactant ranging from 0.1% to 20%, alternatively from 0.1% to 15%, alternatively from 5% to 15%, by weight of the total composition; and a total amount of amphoteric and/or nonionic components, which may range independently from each other from 0.1% to 15%, alternatively from 0.5% to 10%, alternatively from 1% to 8%, by weight of the total composition.

Viscosity

The composition may have a viscosity of from 1000 to 60000 cPs, alternatively from 2000 to 30000 cPs, alternatively from 3000 to 25000 cPs. Viscosity is measured using Brookfield viscometers with cone and plate attachment. For viscosities in the range of 0 to 12000 cPs, the Brookfield DV-11 viscometer with S42 plate is used. 2 ml sample of the composition is equilibrated at 26.7° C. for three minutes before the readings are taken at 1 rpm. For viscosities in the range of 12,000 to 60,000 cPs, the Brookfield DV-1 viscometer with S52 plate is used. 0.5 ml sample of the composition is equilibrated for 1 minute at 26.7° C. before the readings are taken at 1 rpm.

Foam

The compositions of the invention may be provided in the form of foam which is applied to the hair. Foam formation is typically achieved by the use of a foaming agent incorporated within the composition in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides (as described herein); polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

Method for Dyeing Fibers

The present invention also relates to a method for dyeing fibers, wherein the composition according to the present invention is applied to the fibers. The method may be a method for dyeing keratin fibers or synthetic fibers.

The composition may be left on hair for a sufficient amount of time, e.g. from 2 min to 60 min, alternatively 10 min to 40 min. The fibers may then optionally be rinsed using a rinsing composition or water; optionally using a cleansing composition. The fibers may then optionally be treated with a conditioning and/or treating composition and optionally dried.

EXAMPLES

The following are non-limiting examples of compounds or compositions of the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

Exemplified Synthesis of Compounds According to the Present Invention

Example 1

2-(methoxymethyl)-4-{(E)-[2-(methoxymethyl)phenyl]diazenyl}aniline (Formula (1a))

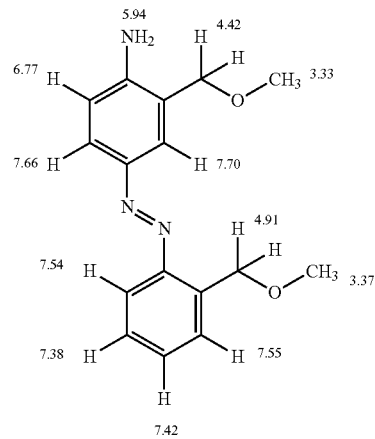

The compound according to formula (1a) has been obtained according to the following experimental protocol.

The following solutions have been prepared:

| First Solution | |
|---|---|
| 600 g | 2-methoxymethylaniline |
| 1.2 l | n-butanol |

| Second Solution | |
|---|---|
| 151 g | sodium nitrite |
| 7.5 g | acrylonitrile |
| 300 ml | water |

The second solution was added to the first solution over a time period of 3 min and 1.05 kg acetic acid was added to the first solution over a time period of 60 min. The first and the second solutions as well as the acetic acid had a temperature of about 0° C. The resulting mixture was stirred for further 60 min at a temperature of about 0° C. to 5° C.

2.10 kg of acetic acid was then added to the resulting mixture at a temperature of about 0° C. to 5° C. over a time period of 60 min. The reaction mixture was then stirred further over a time period of about 4 hours at a temperature of about 10° C. A mixture of 1.5 kg ice and 1.5 kg water was then added. 650 g of sodium acetate was then added to the resulting mixture such that the temperature of the resulting mixture did not exceed 10° C. The reaction mixture was stirred over a further time period of 10 min at a temperature of about 10° C. The resulting mixture was extracted 3 times with 1.2 l ethyl acetate. The extracted layers were combined and washed two times with 1.2 l water. The solvent was then removed under reduced pressure and yielded 563 g of crude material.

The chemical shifts (indicated on the above formula) which are observed on the $^1$HNMR spectrum confirm that the compound which is obtained is the compound of formula (1a).

Example 2

(2-{(E)-[4-amino-3-(hydroxymethyl)-phenyl]diazenyl}-phenyl)methanol (Formula (1b))

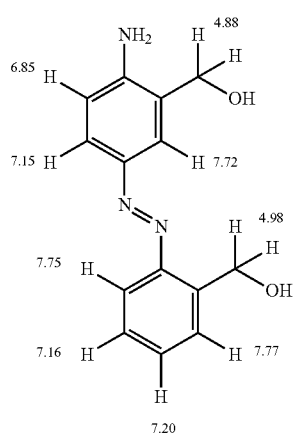 [SMILES: Nc1ccc(/N=N/c2ccccc2CO)cc1CO]

The compound according to formula (1b) has been obtained according to the following experimental protocol.

The following solutions have been prepared:

| First Solution | |
|---|---|
| 5 g | 2-hydroxymethylaniline |
| 15 mL | Hydrogen chloride (25%) |
| 10 mL | water |

| Second Solution | |
|---|---|
| 1.51 g | sodium nitrite |
| 0.075 g | acrylonitrile |
| 10 ml | water |

The second composition was added to the first composition over a time period of 30 min. The first and the second compositions had a temperature of about 0° C. 10.0 g sodium acetate was then added stepwise to the resulting mixture at a temperature of about 5° C. over a time period of 30 min. The resulting mixture was then stirred further over a time period of 30 min at a temperature of about 5° C. The precipitate was then filtrated and washed 3 times with 20.0 mL water and yielded 3.9 g of crude material.

The chemical shifts (indicated on the above formula) which are observed on the $^1$HNMR spectrum confirm that the compound which is obtained is the compound of formula (1b).

Example 3

(2-{(2E)-3-[2-(methoxymethyl)-4-{(E)-[2-(methoxymethyl)-phenyl]diazenyl}phenyl]triaz-2-en-1-yl}phenyl)methanol (Formula (2a))

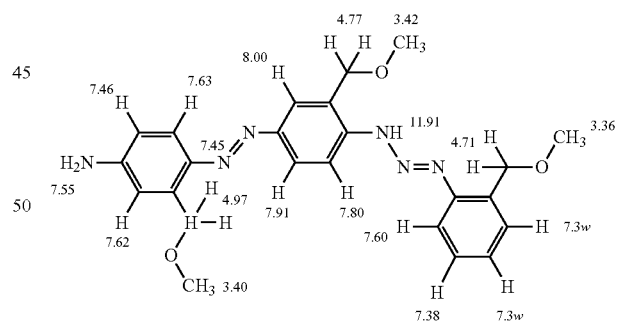

The compound according to formula (2a) has been obtained according to the following experimental protocol.

The following solutions have been prepared:

| First Solution | |
|---|---|
| 1.0 g | 2-methoxymethylaniline |
| 1 ml | water |
| 2 ml | Hydrogen chloride (25%) |

| Second Solution | |
|---|---|
| 540 mg | sodium nitrite |
| 10 ml | water |

| Third Solution | |
|---|---|
| 500 mg | 2-methoxymethylaniline |
| 10 ml | ethanol |

The second solution was added to the first solution over a time period of 3 min. The first and the second solutions had a temperature of about 0° C. The resulting mixture was stirred for further 60 min at a temperature of 0° C. to 5° C.

The third solution was added to the reaction mixture over a time period of 30 min at 0-5° C. The reaction was warmed up to room temperature and stirred for 120 min. A yellowish precipitate was formed, filtrated and dried. The powder was triturated with 4 ml of methanol, filtrated, dried under reduced pressure and yielded 270 mg of orange powder.

The chemical shifts (indicated on the above formula) which are observed on the $^1$HNMR spectrum confirm that the compound which is obtained is the compound of formula (2a).

Example 4

2-(methoxymethyl)-4-{3-[2-(methoxymethyl)phenyl]triaz-1-en-1-yl}aniline (Formula 3a)

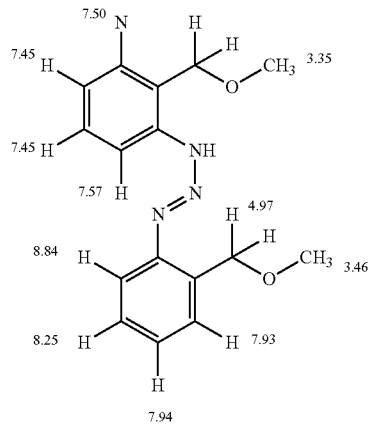 [SMILES: COCc1ccccc1/N=N/Nc1cccc(N)c1COC]

The following solutions have been prepared:

| First Solution | |
|---|---|
| 60 g | 2-methoxymethylaniline |
| 0.122 l | n-butanol |

| Second Solution | |
|---|---|
| 15.1 g | sodium nitrite |
| 0.75 g | acrylonitrile |
| 30.0 ml | water |

The second solution was added to the first solution over a time period of 3 min and 0.11 kg acetic acid was added to the first solution over a time period of 60 min. The first and the second solutions as well as the acetic acid had a temperature of about 0° C. The resulting mixture was stirred for further 60 min at a temperature of about 0° C. to 5° C.

65.0 g of sodium acetate was then added to the resulting mixture such that the temperature of the resulting mixture did not exceed 10° C. The reaction mixture was stirred over a further time period of 10 min at a temperature of about 10° C. The resulting mixture was extracted 3 times with 0.2 l ethyl acetate. The extracted layers were combined and washed two times with 0.2 l water. The solvent was then removed under reduced pressure and yielded 563 g of crude material.

The chemical shifts (indicated on the above formula) which are observed on the $^1$HNMR spectrum confirm that the compound which is obtained is the compound of formula (3a).

Examples of Compositions According to the Present Invention

Three different compositions have been prepared according to the present invention by dissolving 15 mg of a compound according to the present invention in 25 ml of ethanol. Different types of fibers have been treated with these compositions at a temperature of 40° C. The compositions have been applied to different type of fibers. The observed colour intensity results are summarized in the table below.

TABLE 1

Colour intensity results

| Compound | Type of fiber | Colouration result |
|---|---|---|
| 2-(methoxymethyl)-4-{(E)-[2-(methoxymethyl)phenyl]diazenyl}aniline | Cellulose acetate | Intense warm-yellow |
| | Cotton | yellowish |
| | Polyamide | Warm yellow |
| | natural silk | Warm yellow |
| | Viscose | Light yellowish |
| | Wool | Warm yellow |
| | Buffalo hair | Very light yellowish |

TABLE 1-continued

| Compound | Type of fiber | Colouration result |
|---|---|---|
| 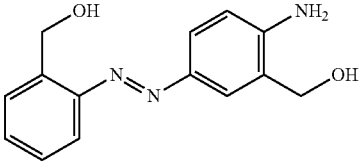<br>(2-{(E)-[4-amino-3-(hydroxymethyl)-phenyl]diazenyl}-phenyl)methanol | Cellulose acetate<br>Cotton<br>Polyamide<br>natural silk<br>Viscose<br>Wool<br>Buffalo hair | Intense warm-yellow<br>yellowish<br>Warm yellow<br>Warm yellow<br>Light yellowish<br>Warm yellow<br>Very light yellowish |
| 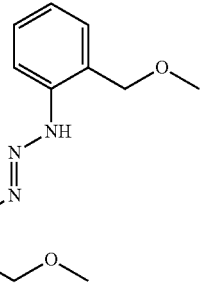<br>(2-{(2E)-3-[2-(methoxymethyl)-4-{(E)-[2-(methoxymethyl)-phenyl]diazenyl}phenyl]triaz-2-en-1-yl}phenyl)methanol | Cellulose acetate<br>Cotton<br>Polyamide<br>natural silk<br>Viscose<br>Wool<br>Buffalo hair | Intense warm-yellow<br>yellowish<br>Warm yellow<br>Warm yellow<br>Light yellowish<br>Warm yellow<br>Very light yellowish |

The dimensions and values disclosed herein are not to be understood as being strictly limited to the exact numerical values recited. Instead, unless otherwise specified, each such dimension is intended to mean both the recited value and a functionally equivalent range surrounding that value. For example, a concentration disclosed as "1%" is intended to mean "about 1%."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition for the dyeing of fibers comprising, in a cosmetically acceptable carrier, at least one compound of formula (I) or (II) or (III):

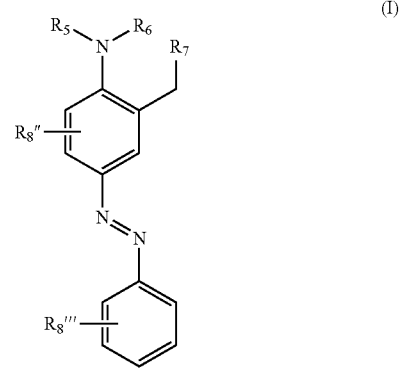

(I)

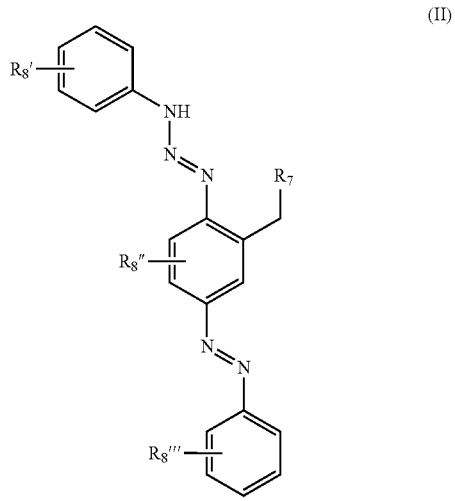

(II)

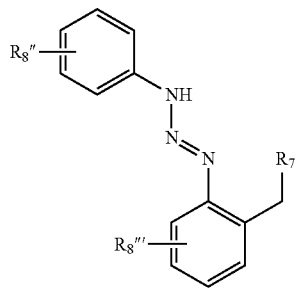

cosmetically acceptable salts thereof or mixtures thereof;
wherein in formula (I), $R_5$ and $R_6$ are selected, independently from each other, from the group consisting of a $C_1$-$C_6$ alkylamino group, a $C_1$-$C_6$ alkylcyano group, a $C_1$-$C_6$ alkyl group, a $C_1$-$C_6$ alkoxy group, a benzyl group, a hydrogen atom, a $C_1$-$C_6$ hydroxyalkyl group, and a $C_4$-$C_6$ polyhydroxyalkyl group, wherein the alkyl groups are linear or branched; and wherein in formula (I) or (II) or (III), $R_7$ is selected from the group consisting of a hydrogen atom, a halogen atom, a $C_1$-$C_6$ alkyl group, a hydroxyl group, a nitro group, a cyano group, an acyl group, an aminoacyl group, and a methoxy group;

wherein in formula (I) or (I) or (III), $R_8'$, $R_8''$ and $R_8'''$ are selected, independently from each other, from the group consisting of a hydrogen atom, a halogen atom, a $C_1$-$C_6$alkyl group, a hydroxyl group, a hydroxylamine group, a nitroso group, a nitro group, a methoxymethyl group, an acyl group, an aminoacyl group, a methoxy group and a hydroxyalkyl group.

2. The composition according to claim 1, wherein the composition is a composition for the dyeing of keratin fibers or synthetic fibers.

3. The composition according to claim 1, wherein the composition is a composition for the dyeing of keratin fibers.

4. The composition according to claim 1, wherein the composition comprises a total amount of compound(s) of formula (I) or (II) or (III) ranging from 0.0001% to 10% by total weight of the composition.

5. The composition according to claim 1, wherein the composition comprises a total amount of compound(s) of formula (I) or (II) or (III) ranging from 0.0001% to 5% by total weight of the composition.

6. The composition according to claim 1, wherein the composition has a pH ranging from 1.5 to 11.

7. The composition according to claim 1, wherein the composition has a pH ranging from 2 to 10.

8. The composition according to claim 1, wherein the composition comprises at least one alkalizing agent.

9. The composition according to claim 8, wherein the alkalizing agent is selected from the group consisting of ammonia, ammonium hydroxide, ammonium carbonate, alkanolamines, guanidium salts, alkali metal hydroxides, alkali metal carbonates and mixtures thereof.

10. The composition according to claim 8, wherein the alkalizing agent is selected from the group consisting of ammonia, ammonium hydroxide, monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof.

11. The composition according to claim 1, wherein the composition comprises at least one oxidizing agent.

12. The composition according to claim 11, wherein the oxidizing agent is selected from the group consisting of hydrogen peroxide, inorganic alkali metal peroxides, organic peroxides, inorganic perhydrate salt bleaching compounds and mixtures thereof.

13. A method for dyeing fibers, wherein the composition as defined in claim 1 is applied to the fibers.

14. The method according to claim 13, wherein the method is a method for dyeing keratin fibers or synthetic fibers.

15. The composition according to claim 1, wherein the compound of formula (I), (II), or (III) comprises at least one methoxymethyl group which is attached to at least one of the phenyl groups.

16. The composition according to claim 1, wherein $R_7$ is selected from the group consisting of hydroxyl group or methoxy group.

17. The composition according to claim 1, wherein $R_7$ is a methoxy group.

18. The composition according to claim 1, wherein the $R_5$ and $R_6$ of formula (I) are selected, independently from each other, from the group consisting of a hydrogen atom and a hydroxyalkyl group.

19. The composition according to claim 1, wherein the compound is selected from the group consisting of:

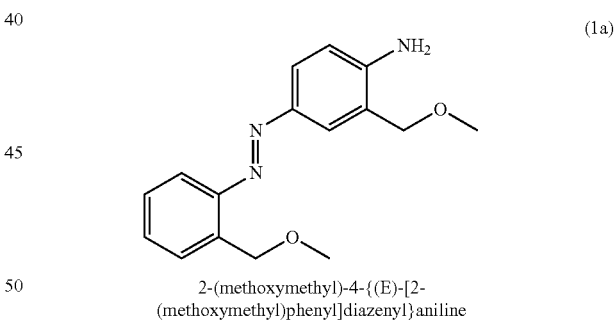

2-(methoxymethyl)-4-{(E)-[2-(methoxymethyl)phenyl]diazenyl}aniline

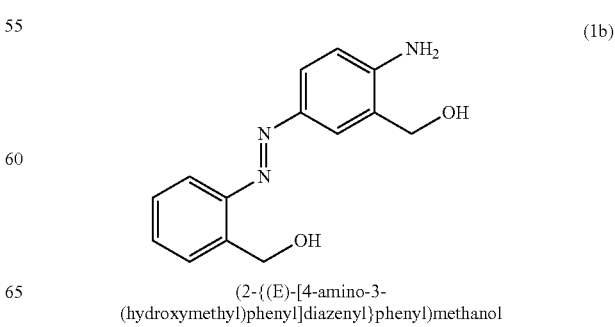

(2-{(E)-[4-amino-3-(hydroxymethyl)phenyl]diazenyl}phenyl)methanol

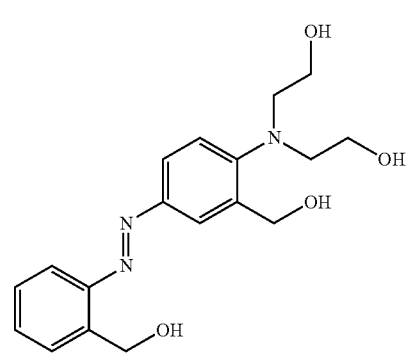
2,2'-{[2-(hydroxymethyl)-4-{(E)-[2-(hydroxymethyl)phenyl]diazenyl}phenyl]imino}diethanol
(1c)
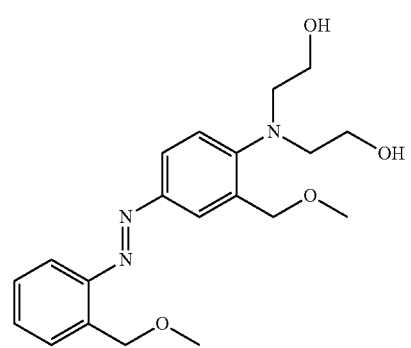
2,2'-{[2-(methoxymethyl)-4-{(E)-[2-(methoxymethyl)phenyl]diazenyl}phenyl]imino}diethanol
(1d)
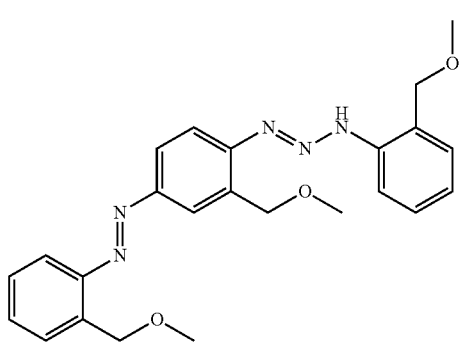
(2-{(2E)-3-[2-(methoxymethyl)-4-{(E)-[2-(methoxymethyl)phenyl]diazenyl}phenyl]triaz-2-en-1-yl}phenyl)methanol
(2a)
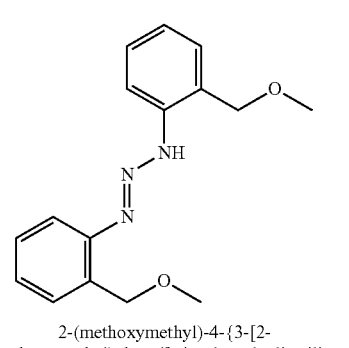
2-(methoxymethyl)-4-{3-[2-(methoxymethyl)phenyl]triaz-1-en-1-yl}aniline.
(3a)
* * * * *